United States Patent [19]

Cesca et al.

[11] 4,017,553

[45] Apr. 12, 1977

[54] PROCESS FOR THE PREPARATION OF LINEAR ALPHA-OLEFIN OLIGOMERS, SUBSEQUENT HYDROGENATION THEREOF AND SATURATED PRODUCTS THUS OBTAINED

[75] Inventors: Sebastiano Cesca; Aldo Priola; Giuseppe Ferraris, all of San Donato Milanese (Milan), Italy

[73] Assignee: Snam Progetti, S.p.A., San Donato Milanese, Italy

[22] Filed: Aug. 1, 1975

[21] Appl. No.: 601,186

[30] Foreign Application Priority Data

Aug. 2, 1974 Italy .................................. 25939/74

[52] U.S. Cl. .................. 260/683.15 D; 260/676 R; 260/683.9
[51] Int. Cl.² .......................................... C07C 3/10
[58] Field of Search .............. 260/683.15 D, 683.9, 260/676 R

[56] References Cited

UNITED STATES PATENTS

| | | | |
|---|---|---|---|
| 3,475,347 | 10/1969 | Johnson | 260/683.15 D |
| 3,887,633 | 6/1975 | Go et al. | 260/683.15 B |

*Primary Examiner*—C. Davis
*Attorney, Agent, or Firm*—Ralph M. Watson

[57] ABSTRACT

The invention relates to the preparation of oligomers starting from linear alpha-olefins and to the subsequent hydrogenation thereof to saturated oligomers products, and more particularly to the catalyst system used in the oligomer preparation reaction, the catalyst system consisting of a first component selected amongst the halogenated organo-metal aluminium components, and a second component capable of reacting with the first one and chosen amongst halogens or interhalogenic compounds and metal halides; thus higher yields of oligomers, as well as an easier performance and a control of the reaction are achieved. In turn the hydrogenation step is carried out in the presence of a known hydrogenation catalyst, at a temperature of 150 to 300° C and under a pressure of from 20 to 150 atmospheres.

16 Claims, No Drawings

PROCESS FOR THE PREPARATION OF LINEAR ALPHA-OLEFIN OLIGOMERS, SUBSEQUENT HYDROGENATION THEREOF AND SATURATED PRODUCTS THUS OBTAINED

The present invention relates to a process for the preparation of oligomers starting from linear alpha-olefins, to the subsequent hydrogenation thereof as well as to the saturated oligomer products thus obtained.

It is known that the paraffinic oils have found, in the last years, a broad application coverage in the feeding and pharmaceutical industry, in the agriculture, as diluents of antiparasitic agents, rubber extenders, plastifiers, lubricating oils.

There are usually obtained by refining suitable fraction of the crude product; however, the recent situation of a poor crude product disposal and the high cost increase have promoted many difficulties in the production of the paraffinic oils.

An alternative way for obtaining said oils is constituted by the cationic oligomerization of linear alpha-olefins, having above all from 3 to 6 carbon atoms, that gives rise to low molecular weight oily products containing residual unsaturations in the chain, which may be lowered through a hydrogenation process producing a saturated product.

However, the known methods, substantially based on the employment of Friedel-Crafts halides, have some remarkable drawbacks, such as the low reaction yields, difficulties in controlling the reaction conditions and, hence, a difficult realization thereof.

We have now found, that is a first object of the present invention, a process for the preparation of linear alpha-olefin oligomers which makes use of a particular catalyst system that, with respect to the ones till now employed, has the advantage of giving higher polymer yields, a more easy performance and reaction control.

By means of the inventive catalyst system it is possible to prepare oligomers starting from linear alpha-olefins having a carbon atom number of from 3 to 12, particularly propylene, butene-1 and pentene-1 oligomers.

It is constituted by two components selected between the two following classes of compounds:

a. an aluminium metallorganic compound having the following general formula

in which X is a halogen atom, R is hydrogen, an alkyl, aryl, cycloalkyl, arylalkyl, alkylaryl, alcoxyl, ester radical having 1 to 12 carbon atoms and $m$ is a number comprised between 1 and $5^3$;

b. a compound able to react with the halides of the preceding class to give the catalytic species which is the starter of the polymerization such compound being selected from the ones belonging to:

I. halogenes or interhalogenic compounds having the general formula X'Y in which X' and Y, the same or different, are selected among chloride, bromine, iodine and fluorine.

II. metal halides having the general formula

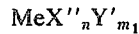

in which X″ is a halogen atom or anion chosen among $ClO_4^-$, $HSO_4^-$, $NO_2^-$, $NO_3^-$, $ClO_3^-$; Y' is oxygen or sulphur or a functional group chosen among the alcoxi, ester, amide, alkyl, cycloalkyl, aromatic, either simple or substituted groups, Me is a metal element chosen among Sn, Si, B, Ge, Pb, Sb, As, Bi and Mg; $m_1$ is a whole number even if equal to zero, $n$ too is a whole number and the sum thereof is equal to the Me valence, apart from Y' is oxygen or sulphur, when the valence is expressed by $2m_1 + n$.

Examples of compounds belonging to the class (a) are $AlEtCl_2$, $AlEt_{1.5}Cl_{1.5}$, $AlEtBr_2$, $AlEt_2Cl$, $AlEt_3$, Al(isopropyl)$_3$, Al(isobutyl)$_3$, etc.

Examples of employable aluminium halides are $AlCl_3$, $AlBr_3$ and $AlI_3$ while compounds belonging to the class (b) are $Cl_2$, $Br_2$, $I_2$, $F_2$, $ICl$, $IBr$, as to the first sub-class and $SnCl_4$, $SiCl_4$, $BCl_3$, $Mg(ClO_4)_2$, $PbCl_4$, $SbCl_5$, $AsCl_5$ etc. as to the second sub-class.

The reaction is carried out in homogeneous phase in a medium generally selected from the hydrocarbons having a carbon atom number from 3 to 12, however, the same may be carried out also without any solvent, when the solvent is constituted by the excess of the monomer.

The two components of the catalyst system may be introduced into the reaction medium in the same moment or it is also possible to add the same separately and the addition order does not affect the obtainable catalytic species; the molar ratio between the component (a) and the component (b) may range from 0.1 to 5, preferably from 0.5 to 2.

The reaction is carried out at temperatures ranging from −30 to +80° C, preferably from −10° to +60° C.

The products, obtained from the polymerization have an average molecular weight varying from 200 to 3000; they contain residual unsaturations that can be expressed as bromine number (bromine grams absorbed from 100 grams of polymer) which is determined according to many methods, from which we draw the one ASTM D 1159.

The unsaturations present at the end of the oligomerization may be reduced or completely decreased through a hydrogenation reaction, constituting a second object of the present invention, which is carried out at temperatures of from 150° to 300° C, at partial hydrogen pressures of from 20 to 150 atmospheres in the presence of hydrogenation catalysts such as, for instance, nickel on Kielesghur, Ni-Raney, Pd on carbon, Pt on carbon.

Possible residual traces of unsaturated products (bromine number of the product lower than 0.1) may be at last removed by passing the compounds on adsorbing silicious earths at temperature of from 50° to 100° C to give the saturated products which constitute the third object of the present invention.

What abovesaid and the working formalities will be more clear by examining the following illustrative examples, the invention must be not thought limited to.

EXAMPLE 1

Use was made of a 300 cc steel autoclave equipped with a magnetic stirrer and thermometric sheath, therein, after a previous drying under vacuum, were introduced under pressure 35 g of butene-1, 50 cm³ of distilled n-pentane and 1.0 mmole (0.105 cc) of $AlEtCl_2$.

The temperature was brought at +15° C and there, under a nitrogen overpressure, a solution was introduced containing 2.0 mmoles of $Cl_2$ diluted in 10 cm³ of n-pentane distilled and cooled at −78° C.

The temperature arose at +32° C. The reaction was prosecuted over 60', then it was stopped by adding methyl alcohol.

The unreacted monomer was then flashed and the resulting product was washed with water added by NaOH in order to remove any catalyst trace, then with distilled water till to neutrality.

The hydrocarbon phase was then distilled in order to completely remove the reaction solvent. G 22.2 were obtained of a dry polymer (yield = 63.5%) having an average osmometric molecular weight $\overline{Mn}$ = 486, an unsaturation content, expressed as bromine number, equal to 31.8 determined according to the method ASTM D 1159 and a residual $Cl_2$ content equal to 522 ppm.

Contemporaneously, according to the same techniques, a standard test was carried out by introducing into the autoclave the same amounts of monomer and solvent and, then, 10 mmole of only $AlEtCl_2$ heat was not developed (T = +15° C). After stopping 0.3 g were obtained (yield = ~0.8%) of a polymer on which it was not possible to determine any property.

The product obtained by using the catalyst system $AlEtCl_2$-$Cl_2$ was then hydrogenated in order to eliminate the unsaturations of the polymeric chain according to the following method: into an autoclave provided with a mechanical stirrer and thermometric heath were introduced 11.17 g of product and 0.75 g of Ni-Raney obtained according to "A. I. Vogel — Practical Organic Chemistry — Longmans, Green & Co., page 870 (1956)".

The temperature was brought to 270° C at a $H_2$ pressure of 80 atmospheres for about 20 hours. Then the whole was cooled, the autoclave was discharged and the hydrogenated product was analyzed as to the residual unsaturations: the bromine number was 0.17.

EXAMPLE 2

Following the formalities of Example 1, the autoclave was charged with the same amounts of monomer, solvent and $AlEtCl_2$.

The reaction was started at +15° C by the addition of a solution containing 1.0 mmole of $Cl_2$ diluted in 10 cm³ of n-pentane distilled and cooled at −78° C.

The temperature increased up to +29° C and the reaction was prosecuted over 60'. G 18.52 of dry product were obtained (yield = 53%) having an average osmometric molecular weight $\overline{Mn}$ = 592, bromine number equal to 32.2 and a $Cl_2$ residual content equal to 418 ppm.

The product thus obtained was hydrogenated according to Example 1: g 13.0 of oligomer were introduced into the autoclave with g 0.87 of Ni-Raney prepared according to Example 1; the temperature was brought to 270° C and the $H_2$ pressure was brought at 90 atm, the reaction being prosecuted over 20 hours. Then the whole was cooled, the autoclave was discharged and the residual unsaturations of the hydrogenated product were determined: bromine number equal to 0.4.

EXAMPLE 3

According to the same formalities of Example 1 the autoclave was charged with the same amounts of monomer, solvent and $AlEtCl_2$, then the reaction was started at +20° C by a solution containing 2.0 mmoles of ICl diluted in 10 cm³ of distilled n-pentane; the temperature increased up to +35° C, and the reaction was prosecuted over 75'. G 19.4 of dry polymer were obtained (yield = 55.4%) having an average numeral molecular weight $\overline{Mn}$ = 820, a bromine number equal to 27.2 and a residual $Cl_2$ content equal to 814 ppm.

The product was hydrogenated according to Example 1, the results being substantially the same.

EXAMPLE 4

According to the formalities of Example 1, the autoclave was charged with the same amounts of monomer, solvent and $AlEtCl_2$ and then the reaction was started by the addition of a solution containing 2.0 mmoles of IBr diluted in 10 cm³ of distilled n-pentane.

The temperature arose from +20 to +26° C and the reaction was prosecuted over 90'. After stopping, g 15.62 of dry product were obtained (yield = 44.6%) having $\overline{Mn}$ = 790 and a bromine number equal to 27.6.

EXAMPLE 5

According to the formalities of Example 1, the autoclave was charged with the same amounts of monomer, solvent and $AlEtCl_2$; then the reaction was started at +20° C by the addition of a solution containing 10 mmoles of $SbCl_5$ diluted in 10 cc of distilled n-pentane; the temperature arose up to +30° C and the reaction continued over 30'.

G 17.1 of dry product were obtained (yield = 48.8%) having $\overline{Mn}$ = 770, bromine number = 28.5 and a $Cl_2$ content = 652 ppm.

EXAMPLE 7

According to Example 1 the autoclave was charged with 70 g of butene-1, 100 cc of distilled n-pentane and 2.0 mmoles of $AlEt_{1.5}Cl_{1.5}$.

The temperature was stabilized at +15° C and a solution was introduced containing 5.0 mmoles of $Cl_2$ in 10 cc of n-pentane distilled and cooled at −78° C; the temperature arose up to +29° C and the reaction prosecuted over 60'.

34.78 g of polymer (yield = 49.7%) were obtained having $\overline{Mn}$ = 564 and a bromine number equal to 34.0.

EXAMPLE 8

According to Example 1 the autoclave was charged with 70 g of butene-1, 100 cc of distilled n-pentane and 2.0 mmoles of $AlEt_2Cl$.

The temperature was stabilized at +18° C and the reaction was started by the addition of a solution containing 6.0 mmoles of $Cl_2$ diluted in 10 cc of n-pentane distilled and cooled at −78° C; the temperature arose up to +24° C and the reaction prosecuted over 45'.

G 35.0 of dry product were obtained (yield = 50%) having $\overline{Mn}$ = 600 and a bromine number = 29.7.

EXAMPLE 9

According to Example 1 the autoclave was charged with 70 g of butene-1, 100 cm³ of distilled n-pentane and 2.0 mmoles of $AlEt_3$. Then the reaction was started by the addition, at +15° C, of a solution containing 8.0 mmoles of $Cl_2$ diluted in 10 cc of n-pentane distilled and cooled at −78° C; the temperature arose up to +30° C and the reaction prosecuted over 60'.

G 33.0 of dry product were obtained (yield = 47.2%) having $\overline{Mn}$ = 658 and a bromine number equal to 31.9.

EXAMPLE 10

According to Example 1 the autoclave was charged with 35 g of butene-1, 50 cm³ of distilled n-pentane and 1.0 mmole of $AlEtCl_2$. Then the reaction was started by the addition, at +14° C, of 0.64 mmole of $Mg(ClO_4)_2$ suspended in 10 cc of distilled n-pentane: the temperature arose up to +20° C and the reaction prosecuted for 17 hours.

G 7.40 of dry product were obtained (yield = 21.1%) having $\overline{M}n = 720$, bromine number = 20.8.

What we claim is:

1. Process for the preparation of oligomers from linear alpha-olefins having a carbon atom number of from 3 to 12 characterized in that the reaction is carried out in the presence of a catalyst system constituted by:
   a. an aluminum metallorganic halide compound having the following general formula $$R_mAlX_{3-m}$$

in which X is a halogen atom, R is hydrogen, an alkyl, aryl, cycloalkyl, arylalkyl, alkylaryl, alkoxy, ester radical having 1 to 12 carbon atoms and $m$ is a number comprised between 1 and 3;
   b. A compound able to react with the halide of (a) to give the catalytic species which is the starter of the polymerization such compound being selected from the group consisting of:
      I. halogens or interhalogenic compounds having the general formula X'Y in which X' and Y, the same or different, are selected among chlorine, bromine, iodine and fluorine,
      II. metal halides having the general formula $$MeX''_nY'_{m_1}$$

in which X'' is a halogen atom or anion chosen among $ClO_4^-$, $HSO_4^-$, $NO_2^-$, $NO_3^-$, $ClO_3^-$, Y' is oxygen or sulphur, or a functional group chosen among the alcoxi, ester, amide, alkyl, cycloalkyl, aromatic, either simple or substituted, groups, Me is a metal element chosen among Si, B, Be, Sb, As, Bi and Mg; $m_1$ is a whole number, even if equal to zero, $n$ too is a whole number and the sum thereof is equal to the Me valence, apart from Y' is oxygen or sulphur, where the valence is expressed by $2m_1 + n$.

2. Process according to claim 1 characterized in that the reaction is carried out in presence of a suspension medium selected from the hydrocarbons having a carbon atom number of from 3 to 12.

3. Process according to claim 1 characterized in that the reaction is carried out without any solvent.

4. Process according to claim 1 characterized in that the reaction is carried out at a molar ratio between (a) and (b) ranging from 0.1 to 5, preferably from 0.5 to 2.

5. Process according to claim 1 characterized in that the reaction is carried out at temperatures ranging from −30° to +80° C.

6. Process for the removal of unsaturations from oligomers obtained by the process of claim 1 consisting in contacting the unsaturated products with a hydrogenation catalyst at temperatures of from 150° to 300° C, at partial hydrogen pressures of from 10 to 150 atmospheres and, eventually, in passing the product thus obtained onto absorbing siliciuous earths at temperatures ranging from 50° to 100° C.

7. Saturated oligomer products when obtained according to the process of claim 6.

8. Process according to claim 1 wherein the metal in the metal halide is Si.

9. Process according to claim 1 wherein the metal in the metal halide is B.

10. Process according to claim 1 wherein the metal in the metal halide is Be.

11. Process according to claim 1 wherein the metal in the metal halide is Sb.

12. Process according to claim 1 wherein the metal in the metal halide is As.

13. Process according to claim 1 wherein the metal is the metal halide is Bi.

14. Process according to claim 1 wherein the metal is the metal halide is Mg.

15. Process according to claim 5 characterized in that the reaction is carried out at temperatures between −10° to +60° C.

16. Process for the preparation of oligomers from linear alpha-olefins having a carbon number of from 3 to 12 characterized in that the reaction is carried out in the presence of a catalyst system constituted by:
   a. an aluminum metallorganic halide compound having the following general formula $$R_mAlX_{3-m}$$

in which X is a halogen atom, R is hydrogen, an alkyl, aryl, cycloalkyl, arylalkyl, alkylaryl, alkoxy, ester radical having 1 to 12 carbon atoms and $m$ is a number comprised between 1 and 3;
   b. a compound able to react with the halide of (a) to give the catalytic species which is the starter of the polymerization such compound being selected from the group consisting of halogens or interhalogenic compounds having the general formula X'Y in which X' and Y are the same or different and are selected from the group consisting of chlorine, bromine, iodine and fluorine.

* * * * *

UNITED STATES PATENT AND TRADEMARK OFFICE
CERTIFICATE OF CORRECTION

PATENT NO. : 4,017,553
DATED : April 12, 1977
INVENTOR(S) : Sebastiano Cesca et al.

It is certified that error appears in the above-identified patent and that said Letters Patent are hereby corrected as shown below:

Page one of the patent after "Assignee:" rewrite

Snam Progetti as --Snamprogetti--

Signed and Sealed this sixteenth Day of August 1977

[SEAL]

Attest:

RUTH C. MASC
Attesting Officer

C. MARSHALL DANN
Commissioner of Patents and Trademarks